US00PP33434P2

(12) United States Plant Patent
van Kesteren

(10) Patent No.: US PP33,434 P2
(45) Date of Patent: Aug. 31, 2021

(54) ***DELPHINIUM* PLANT NAMED 'COADELPNK'**

(50) Latin Name: ***Delphinium* hybrid**
Varietal Denomination: COADELPNK

(71) Applicant: Anthony Paul Coakley, Glasgow (GB)

(72) Inventor: Marc van Kesteren, Noordwijkerhout (NL)

(73) Assignee: Anthony Paul Coakley, Glasgow (GB)

( * ) Notice: Subject to any disclaimer, the term of this patent is extended or adjusted under 35 U.S.C. 154(b) by 0 days.

(21) Appl. No.: 17/077,590

(22) Filed: Oct. 22, 2020

(51) Int. Cl.
*A01H 5/02* (2018.01)
*A01H 6/72* (2018.01)

(52) U.S. Cl.
USPC ..... Plt./423
CPC ..... *A01H 6/72* (2018.05)

(58) Field of Classification Search
USPC ..... Plt./423
CPC ..... A01H 6/72; A01H 5/02
See application file for complete search history.

*Primary Examiner* — Keith O. Robinson
(74) *Attorney, Agent, or Firm* — Samuel R. McCoy, Jr.

(57) ABSTRACT

A new and distinct *Delphinium* hybrid plant named 'COADELPNK' which is characterized by an abundance of basal foliage with a compound terminal raceme held within and above the foliage, flowers loosely held on long pedicels, flowers with an abundance of tepaloids, a unique color appearance of the perianth comprised of a light green center which becomes progressively more suffused with a dark pink general coloration towards the outer whorls of the perianth, and the stability and uniformity of these traits through successive cycles of asexual propagation.

3 Drawing Sheets

Latin name of the genus and species: The Latin name of the genus and species of the novel variety disclosed herein is *Delphinium* hybrid.

Variety denomination: The inventive variety of *Delphinium* disclosed herein has been given the variety denomination 'COADELPNK'.

BACKGROUND OF THE INVENTION

Parentage: The claimed plant originated as a naturally occurring, whole-plant mutation of *Delphinium* hybrid 'Coadelbol' (U.S. Plant Pat. No. 27,704). In the summer of 2012 the inventor discovered the mutation at a commercial greenhouse in Noordwijkerhout, Netherlands, growing amongst a crop of *Delphinium* hybrid 'Coadelbol'. The mutation was noted for its compact growth habit, abundance of flowers and unique pink flower color. The new plant was subsequently isolated for further evaluation in order to confirm the distinctness and stability of the characteristics first observed.

Asexual Reproduction: In the spring of 2013, 'COADELPNK' was first asexually reproduced in Glasgow, Scotland by way of softwood stem cuttings. The claimed plant was later asexually reproduced by way of meristematic tissue culture. The claimed plant was found to asexually reproduce in uniform and stable manner and four successive cycles of vegetative propagation have proven to be true to type.

SUMMARY OF THE INVENTION

The following characteristics have been repeatedly observed and represent the distinguishing characteristics of the new *Delphinium* plant, 'COADELPNK'. These traits, in combination, distinguish 'COADELPNK' as a new and distinct cultivar.

1. 'COADELPNK' exhibits a compact growth habit with an abundance of basal foliage and a compound terminal raceme held within and above the foliage; and
2. 'COADELPNK' exhibits flowers loosely held on long pedicels along the raceme; and
3. 'COADELPNK' exhibits an abundance of tepaloids; and
4. 'COADELPNK' exhibits flowers with multiple whorls of very tightly held tepaloids at the center of the perianth, more relaxed tepaloids towards the outer whorls of the perianth, and an outer whorl of loosely held tepals; and
5. 'COADELPNK' exhibits light purple tepals and tepaloids when fully opened which generally appear as a dark pink coloration; and
6. 'COADELPNK' exhibits innermost tepaloids at and near the center of the perianth which are light yellow-green; and
7. 'COADELBOL' exhibits a unique color appearance of the perianth comprised of a light green center, becoming progressively more suffused with dark pink towards the outer whorls of the perianth.

BOTANICAL DESCRIPTION OF THE PLANT

Figure 1:
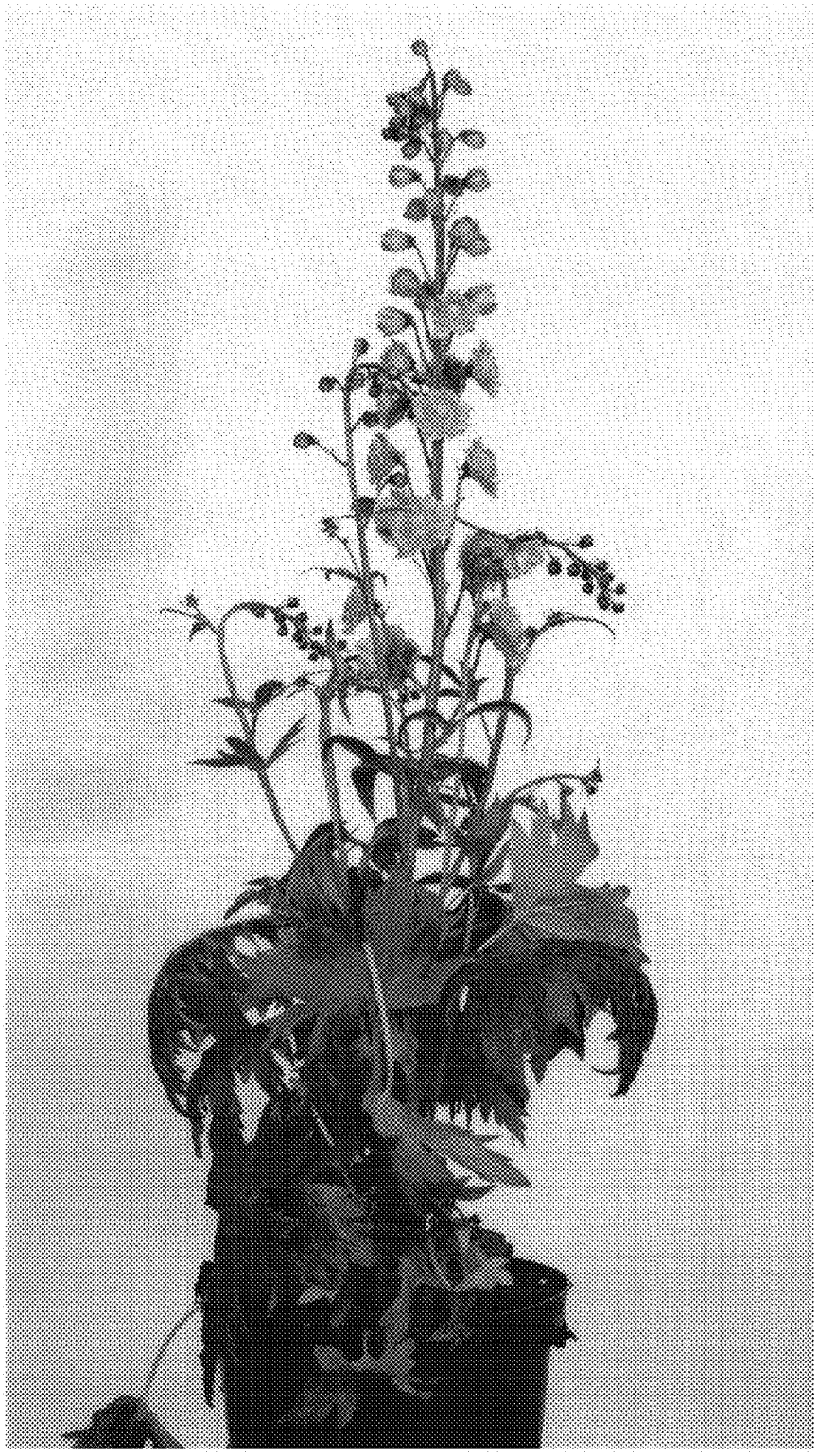
FIG. 1 illustrates, as nearly true as it is reasonably possible to make the same in color photographs of this type, an exemplary 'COADELPNK' plant at approximately 6 months of age grown in Glasgow, Scotland.
Figure 2:
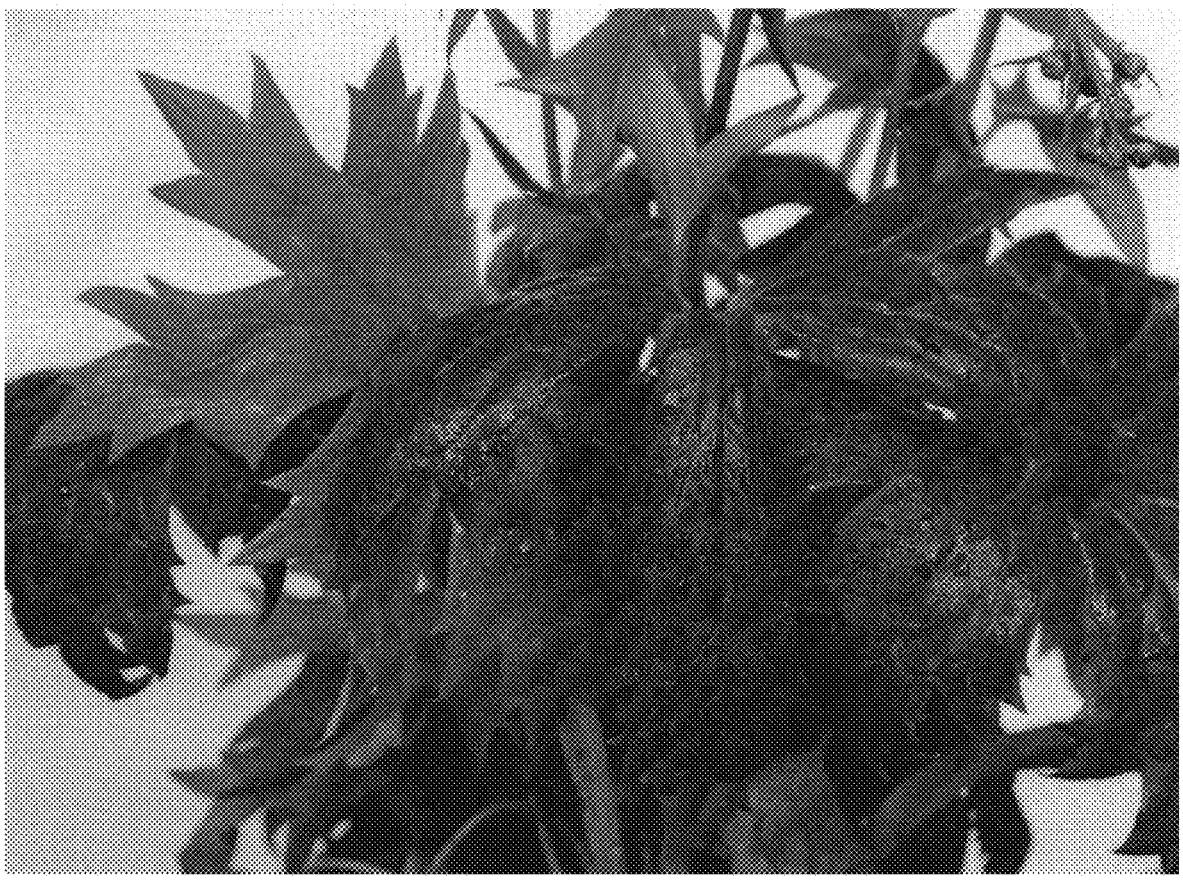
FIG. 2 illustrates, as nearly true as it is reasonably possible to make the same in color photographs of this type, the foliage of 'COADELPNK'.
Figure 3:
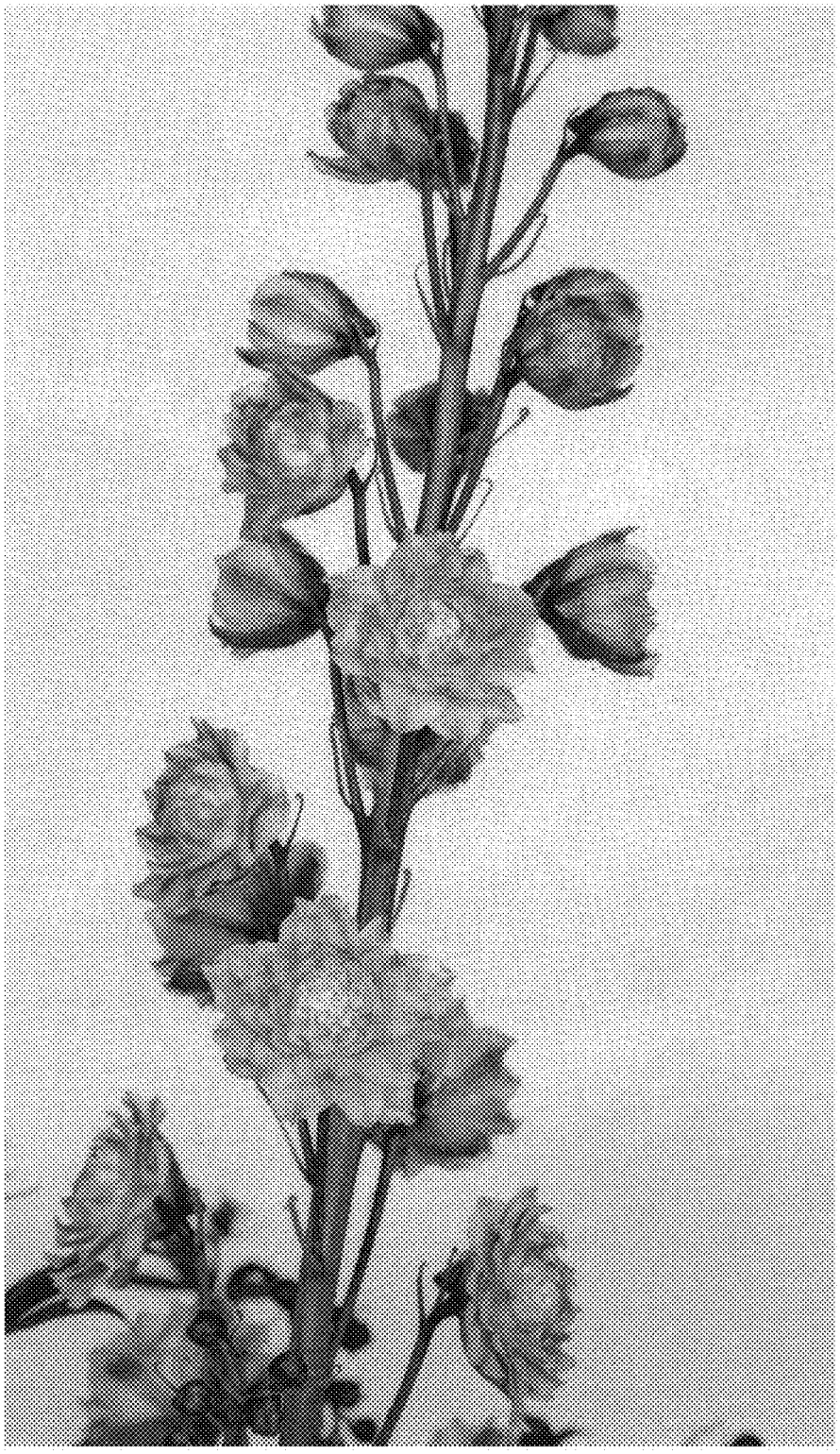
FIG. 3 illustrates, as nearly true as it is reasonably possible to make the same in color photographs of this type, the flowers of 'COADELPNK'.

The following is a detailed botanical description of a new and distinct *Delphinium* plant known as 'COADELPNK'. Plant observations were made on a 6 month-old plant growing in Glasgow, Scotland. The observed plant was field-grown in full exposure to natural sunlight, maintained with organic fertilizer and overhead irrigation. Chemical control of powdery mildew was utilized in production but no other pest or pathogen countermeasures were employed. For the purposes of these observations, the observed plant was harvested from the field and potted into a 19 cm nursery container. Observation data was recorded in July of 2020.

Those skilled in the art will appreciate that certain characteristics will vary with older or, conversely, younger plants. 'COADELPNK' has not been observed under all possible environmental conditions. Where dimensions, sizes, colors and other characteristics are given, it is to be understood that such characteristics are approximations or averages set forth as accurately as practicable. The phenotype of the variety may vary with variations in the environment such as season, temperature, light intensity, day length, cultural conditions and the like. Color notations are based on *The Royal Horticultural Society Colour Chart,* The Royal Horticultural Society, London, Sixth Edition except where common terms of color are used.

A botanical description of 'COADELPNK' and comparisons with the parent and most similar commercial cultivar are provided below.

General plant description:

*Plant habit*.—Perennial plant with basal foliage and branched flowering stems, bearing flowers arranged on terminal racemes held within and above the foliage.

*Plant profile*.—Narrow ovate to ovate.

*Height*.—36.8 cm to the top of the foliar plane; 76.0 cm to the top of the floral plane.

*Spread*.—36.3 cm.

*Plant vigor*.—Moderately vigorous.

*Growth rate*.—Moderately fast growing.

*Propagation*.—Method — Softwood stem cuttings. Time to initiate rooting — 6 weeks at an average ambient temperature of 15 degrees Celsius. Time to produce flowering plant from rooted cutting — Approximately 6 months in an 11 cm container.

*Pest resistance and susceptibility*.—Not any more or less susceptible to pests or diseases known to effect *Delphinium* sp.

*Environmental tolerances*.—Adapt to, at least, USDA Zones 5 to 9 and temperatures ranging from minus 23 degrees Celsius to 35 degrees Celsius; moderate tolerance to rain; low tolerance to wind.

Root system:

*Description*.—A moderately dense network of relatively shallow thin, fibrous feeder roots and deeper thick anchor roots.

Stems:

*Branching habit*.—No vegetative branches are present, however branched flowering stems are present.

*Flowering stem*.—Quantity — Three. Attitude — Erect; near vertical. Aspect — Generally rounded; slightly angular. Strength — Strong. Length — 10.0 cm. Diameter — 1.2 cm. Internode length — 1.8 cm. Texture — Sparsely pubescent; hairs are 0.1 cm on average and are colored a translucent white, nearest to RHS NN155C. Luster — Matte, due to the presence of epicuticular wax. Color, developing stems — Yellow-green, nearest to RHS 146C, and covered with an epicuticular wax which is colored yellow-green, nearest to in between RHS 145A and 146D. Color, mature stems — Green, nearest to a combination of RHS 143A, 143B, and 143C. Stems are covered with an epicuticular wax which is colored nearest to in between yellow-green and greyed-green, RHS 147C and 191B. Color at the internodes — Green, nearest to a combination of RHS 143A, 143B, and 143C. Stems are covered with an epicuticular wax which is colored nearest to in between yellow-green and greyed-green, RHS 147C and 191B.

Foliage:

*Arrangement*.—Alternate.

*Attachment*.—Petiolate.

*Division*.—Simple.

*Quantity*.—13 stem leaves.

*Shape*.—Palmate with a reniform outline; deeply lobed to near cleft.

*Lobes*.—Depth of sinuses — Deep. Sinus orientation — Divergent.

*Aspect*.—Slightly convex and reflexed.

*Attitude*.—Outward.

*Length*.—17.2 cm.

*Width*.—20.7 cm.

*Apex*.—Narrowly acute.

*Base*.—Hastate; lobes free to touching.

*Margins*.—Coarsely serrate.

*Texture and pubescence, adaxial surface*.—Smooth and glabrous.

*Texture and pubescence, abaxial surface*.—Smooth and glabrous.

*Luster, adaxial surface*.—Matte.

*Luster, abaxial surface*.—Matte.

*Color*.—Juvenile foliage color, adaxial surface — Yellow-green, nearest to RHS 144A. Juvenile foliage color, abaxial surface — Yellow-green, nearest to RHS 144B. Mature leaf color, adaxial surface — Green, nearest to RHS NN137A yet slightly darker. Mature leaf color, abaxial surface — Yellow-green, nearest to RHS 147B.

*Venation*.—Type — Laciniate. Vein color, adaxial surface — Yellow-green, nearest to RHS 144A. Vein color, abaxial surface — Yellow-green, nearest to RHS 144B.

*Petiole*.—Length — 9.3 cm. Diameter — Petioles are flattened; 0.4 cm tall and 0.5 cm wide. Strength — Very strong. Texture, adaxial and abaxial surfaces — Smooth and glabrous. Luster, adaxial and abaxial surfaces — Moderately glossy. Color, adaxial and abaxial surface — Yellow-green, nearest to RHS 144A.

*Stipules*.—Absent.

Inflorescence:

*Inflorescence type*.—Compound terminal raceme with a central, main raceme and multiple lateral racemes.

*Natural flowering season*.—Late summer in Glasgow, Scotland.

*Time to flower or response time*.—Approximately 10 months.

*Height*.—The entire compound raceme is 61.5 cm high, from the lowest branching of the peduncle to the apex of the inflorescence. The main, central raceme is 42.9 cm tall.

*Diameter*.—The entire compound raceme is 23.9 cm in diameter; the main, central raceme is 10.3 cm in diameter.

*Quantity of flowers per inflorescence*.—140 on the entire compound raceme; 34 on the main raceme.

*Peduncle*.—Length — Approximately 41.1 cm. Diameter — Approximately 0.6 cm. Attitude — Erect, in an average angle of 0 degrees to the main stem. Strength — Strong. Texture — Smooth and glabrous. Luster — Slightly glossy. Color — Yellow-green, nearest to in between RHS 144A and 146B.

*Bracts*.—Quantity — Two bracts are present at the base of each individual flower. Shape — Linear. Length — 1.5 cm, on average. Width — 0.175 cm, on average. Apex — Narrowly acute. Base — Cuneate. Margin — Entire. Texture — Smooth and sparsely covered with short, soft hairs with an average length of 0.03 cm and colored white, nearest to RHS NN155C. Color, adaxial and abaxial surfaces — Yellow-green, nearest to RHS 144B.

Flower bud:

*Shape*.—Obovate.

*Length*.—Average of 1.4 cm.

*Diameter*.—0.8 cm tall and 1.0 cm wide.

*Texture*.—Smooth and sparsely pubescent; soft white hairs are approximately 0.03 cm long and colored a translucent white, nearest to RHS NN155C.

*Luster*.—Slightly glossy.

*Color, upper surface*.—Purple, nearest to RHS N77D, and fading darker towards the proximal end, nearest to RHS N79A.

*Color, lower surface*.—Yellow-green, nearest to RHS 145C.

Flower:

*Type and form*.—Rotate; double.

*Aspect*.—Outward.

*Flowering habit*.—Freely flowering.

*Flower longevity on plant*.—Approximately 10 days.

*Longevity of cut flowers*.—Approximately 10 days.

*Persistent or self-cleaning*.—Self-cleaning.

*Fragrance*.—Non-fragrant.

*Diameter*.—Average of 4.4 cm.

*Perianth*.—No distinct petals and sepals, only tepals and tepaloids are present. Tepals — Quantity — 5 unfused tepals; one dorsal, two lateral, and two lower tepals. Arrangement — Rotate; single whorl. Attitude — Relaxed. Aspect — Moderately concave. Length — Dorsal tepal — 2.4 cm. Lateral tepals — 2.3 cm. Lower tepals — 2.4 cm. Width — Dorsal tepal — 1.5 cm. Lateral tepals — 1.6 cm. Lower tepals — 1.55 cm. Shape — Dorsal tepal is broad ovate; lateral tepals are elliptic; and, lower tepals are broad obovate. Apex — All tepals are acute. Base — All tepals are broad cuneate. Margin — All tepals are entire and moderately undulated. Texture, luster and pubescence of the upper surface — All tepals are glabrous, slightly velvety, and matte. Texture, luster and pubescence of the lower surface — All tepals are moderately covered with very short, soft hairs with an average length of 0.3 cm and colored white, nearest to RHS NN155C. All tepals are matte. Color when opening, upper surface — Dorsal tepal — Greyed-purple, nearest to RHS 186D, and fading to yellow-green towards the base, nearest to RHS 144C; distally suffused with yellow-green, nearest to RHS 146C. Lateral tepals — Greyed-purple, nearest to RHS 186D, and fading to yellow-green towards the base, nearest to RHS 144C; distally suffused with yellow-green, nearest to RHS 146C. Lower tepals — Greyed-purple, nearest to RHS 186D, and fading to yellow-green towards the base, nearest to RHS 144C; distally suffused with yellow-green, nearest to RHS 146C. Color when opening, lower surface — Dorsal tepal — Nearest to in between greyed-red and greyed-purple, nearest to RHS 182C and 186C; apex is yellow-green, nearest to RHS 146C. Lateral tepals — Purple, nearest to RHS 75B, and fading to yellow-green towards the base, nearest to RHS 145C; apex is yellow-green, nearest to RHS 146C. Lower tepals — Purple, nearest to RHS 75B, and fading to yellow-green towards the base, nearest to RHS 145C; apex is yellow-green, nearest to RHS 146C. Color when fully opened, upper surface — Dorsal tepal — Nearest to in between greyed-purple and purple, RHS 76B and 186C, and fading to yellow-green towards the base, nearest to a mixture of RHS 145A and 145B; lightly suffused with yellow-green, nearest to RHS 146C, towards the apex. Tepals do not fade with age. Lateral tepals — Purple, nearest to RHS 76B, and fading to yellow-green towards the base, nearest to a mixture of RHS 145B and 145C; lightly suffused with yellow-green towards the apex, nearest to RHS 146C. Tepals do not fade with age. Lower tepals — Purple, nearest to RHS 76B, and fading to yellow-green towards the base, nearest to a mixture of RHS 145B and 145C; lightly suffused with yellow-green, nearest to RHS 146C, towards the apex. Tepals do not fade with age. Color when fully opened, lower surface — Dorsal tepal — Greyed-red, nearest to RHS 181D yet lighter; fading to green towards the base, nearest to a mixture of RHS 136A and 136B; suffused with yellow-green towards the apex, nearest to RHS 146C. Tepals do not fade with age. Lateral tepals — Purple, nearest to RHS 76B, and fading to yellow-green towards the base, nearest to a mixture of RHS 145A, 145B and 145C; lightly suffused with yellow-green, nearest to RHS 146C, centrally and also towards the apex. Tepals do not fade with age. Lower tepal — Violet-blue, nearest to RHS 94B, and fading to yellow-green towards the base, nearest to RHS 144B; a yellow-green blotch is present near the apex, nearest to in between RHS 146C and 146D. Tepals do not fade with age. Tepal venation color — Green, nearest to RHS 136A. Fully opened, lower surface — Greyed-green, nearest to RHS N189A. Tepaloids — Arrangement — Rotate; the unfused tepaloids are relatively tightly-held in 10 whorls. Attitude — Erect. Aspect — Strongly concave. Quantity — 65. Length — 2.0 cm. Width — 1.0 cm. Shape — Obovate. Apex — Acute. Base — Broad cuneate. Margin — Entire; moderately to heavily undulated. Texture, luster and pubescence of the inner surface — Moderately velvety, glabrous and slightly glossy. Texture, luster and pubescence of the outer surface — Slightly velvety, glabrous and matte.

Color when opening, upper surface — Outer tepaloids are yellow-green, nearest to RHS 145D, with a darker central blotch, nearest to a mixture of RHS 145B and 145C; apex is suffused with purple, nearest to a mixture of RHS 75B and 75C. Inner tepaloids are green-white, nearest to RHS 157D yet lighter, and fading to yellow-green at the apex, nearest to RHS 145B. Color when opening, lower surface — Outer tepaloids are yellow-green, nearest to RHS 145D, with a darker central blotch, nearest to a mixture of RHS 145B and 145C; apex is suffused with purple, nearest to RHS 76B. Inner tepaloids are green-white, nearest to RHS 157D yet lighter, and fading to yellow-green at the apex, nearest to RHS 145B. Color when fully opened, upper surface — Outer tepaloids are yellow-green at the base, nearest to RHS 145D, and progressively suffused with purple distally, nearest to a mixture of RHS 75B, 75C and 75D; apex and distal margins are purple, nearest to a mixture of RHS 75B, 75C and 75D; a yellow-green central blotch is present, nearest to RHS 145C. Inner tepaloids are green-white, nearest to RHS N157D, and progressively suffused with yellow-green towards and at the apex, nearest to RHS 145B. Tepaloids do not fade with age. Color when fully opened, lower surface — Outer tepaloids are yellow-green at the base, nearest to RHS 145D, and progressively suffused with purple distally, nearest to a mixture of RHS 75B, 75C and 75D; apex and distal margins are purple, nearest to a mixture of RHS 75B, 75C and 75D; a yellow-green central blotch is present, nearest to RHS 145C. Inner tepaloids are green-white, nearest to RHS N157D, and progressively suffused with yellow-green towards and at the apex, nearest to RHS 145B. Tepaloids do not fade with age. Tepaloid venation color when fully opened, inner surface — Yellow-green, nearest to RHS 145A. Tepaloid venation color when fully opened, outer surface — Yellow-green, nearest to RHS 144B. Pedicels — Length — 6.3 cm. Diameter — 0.2 cm. Angle — Average angle to peduncle axis is approximately 30 degrees. Strength — Moderately strong to strong. Texture — Smooth and glabrous. Luster — Moderately glossy. Color — Yellow-green, nearest to in between RHS 144A and 146B. Spurs — Quantity — One dorsal tepal spur present. Length — 0.5 cm. Diameter — 0.4 cm. Shape — Broad oblong. Apex — Obtuse. Base — Broad cuneate. Texture — Moderately rugose and glabrous. Luster — Moderately glossy. Color — Yellow-green, nearest to RHS 148A.

Reproductive organs: All reproductive organs reduced to tepaloids. An undeveloped ovary is present; colored yellow-green, nearest to RHS 147A yet darker.

Fruit and seed: No fruiting has been observed.

Comparison With the Parent Plant

Plants of the new cultivar 'COADELPNK' differ from the parent, *Delphinium* hybrid 'COADELBOL' (U.S. Plant Pat. No. 27,704), by the characteristics described in Table 1.

TABLE 1

| Characteristic | 'COADELPNK' | 'COADELBOL' |
|---|---|---|
| Plant size. | Smaller than 'COADELBOL'. | Larger than 'COADELPNK'. |
| Abundance of foliage. | More abundant than 'COADELBOL'. | Less abundant than 'COADELPNK'. |
| Inflorescence type. | Compound terminal raceme. | Unbranched terminal raceme. |
| Inflorescence size. | Larger than 'COADELBOL'. | Smaller than 'COADELPNK'. |
| General appearance of the inflorescence. | Flowers appear to be more loosely held on the raceme due to longer flower pedicels. | Flowers appear to be more tightly held on the raceme due to shorter flower pedicels. |
| Tepaloid arrangement within the perianth. | Tepaloids are more tightly held in whorls. | Tepaloids are more loosely held in whorls. |
| Quantity of tepaloids. | More than 'COADELBOL'. | Less than 'COADELPNK'. |
| General coloration of the outer tepaloids when fully opened. | Light purple, generally appearing as a dark pink coloration. | Central zone of the tepaloids are violet; marginal zone is violet blue. |

Comparison With the Most Similar *Delphinium* Cultivar Known to the Inventor

Plants of the new cultivar 'COADELPNK' are most similar to the commercial cultivar, *Delphinium* hybrid 'COADELBBL' (a United States Patent application for which is being filed concurrently with the instant application). A comparison of 'COADELPNK' with *Delphinium* 'COADELBBL' is described in Table 2.

TABLE 2

| Characteristic | 'COADELPNK' | 'COADELBBL' |
|---|---|---|
| Growth habit. | Flowering stems are shorter and held within and above the foliage. | Flowering stems are longer and held within and above the foliage. |
| Quantity of flowering stems. | More than 'COADELBBL'. | Fewer than 'COADELPNK'. |
| Length of flowering stem. | Shorter than 'COADELBBL'. | Longer than 'COADELPNK'. |
| Inflorescence size. | Larger than 'COADELBBL'. | Smaller than 'COADELPNK'. |
| General coloration of the tepals and outer tepaloids when fully opened. | Light purple, generally appearing as a dark pink coloration. | Light greyed-red to greyed-purple, generally appearing as a light pink coloration. |
| Expression of color on the tepaloids. | More prominent than 'COADELBBL'. | More conspicuous than 'COADELPNK'. |
| Quantity of tepaloids. | More than 'COADELBBL'. | Fewer than 'COADELPNK'. |

That which is claimed is:

1. A new and distinct variety of *Delphinium* hybrid plant named 'COADELPNK', substantially as described and illustrated herein.

* * * * *